United States Patent [19]

Porter

[11] 4,210,029
[45] Jul. 1, 1980

[54] DIFFERENTIAL FIBER OPTIC DIFFERENTIAL PRESSURE SENSOR

[75] Inventor: John H. Porter, Colchester Point, Vt.

[73] Assignee: Lad Research Industries, Inc., Burlington, Vt.

[21] Appl. No.: 36,246

[22] Filed: May 4, 1979

[51] Int. Cl.² .......................... G01L 7/08; G01L 9/00
[52] U.S. Cl. .................................. 73/705; 73/723; 128/634; 128/673; 128/748
[58] Field of Search .................... 73/705, 723, 731; 128/634, 673, 748

[56] References Cited

U.S. PATENT DOCUMENTS

| | | | |
|---|---|---|---|
| 3,503,116 | 3/1970 | Strack | 73/705 |
| 3,580,082 | 5/1971 | Strack | 73/705 |
| 3,686,958 | 8/1972 | Porter et al. | 73/705 |
| 3,789,667 | 2/1974 | Porter et al. | 73/705 |

Primary Examiner—Donald O. Woodiel
Attorney, Agent, or Firm—W. R. Hulbert

[57] ABSTRACT

A differential sensor unit precisely monitors ambient pressure within a confined space, such as blood pressure or intracranial pressure of a human patient, utilizing fiber optic light guides. Three light guides pass within a pneumatic line into one end of a rigid cylindrical envelope which may be inserted into a vein or artery or implanted in the skull. The other end of the envelope is bounded by a flexible membrane. Of the external ends of the guides, one faces a light source and each of the others faces a light detector. A reflective surface is attached to the internal face of the flexible membrane. Within the envelope the internal ends of the light guides face the reflective surface and are arranged to respond to movement of the flexible membrane due to differential pressure change across the membrane so that motion of the reflective surface relative to the internal ends varies the light transmitted from the first light guide to the others and consequently varies the light intensity sensed by each detector. The detectors can be arranged to actuate pressure display and pneumatic controls acting through the pneumatic line to adjust the internal pressure of the envelope to match the surrounding pressure and thereby measure that pressure.

4 Claims, 7 Drawing Figures

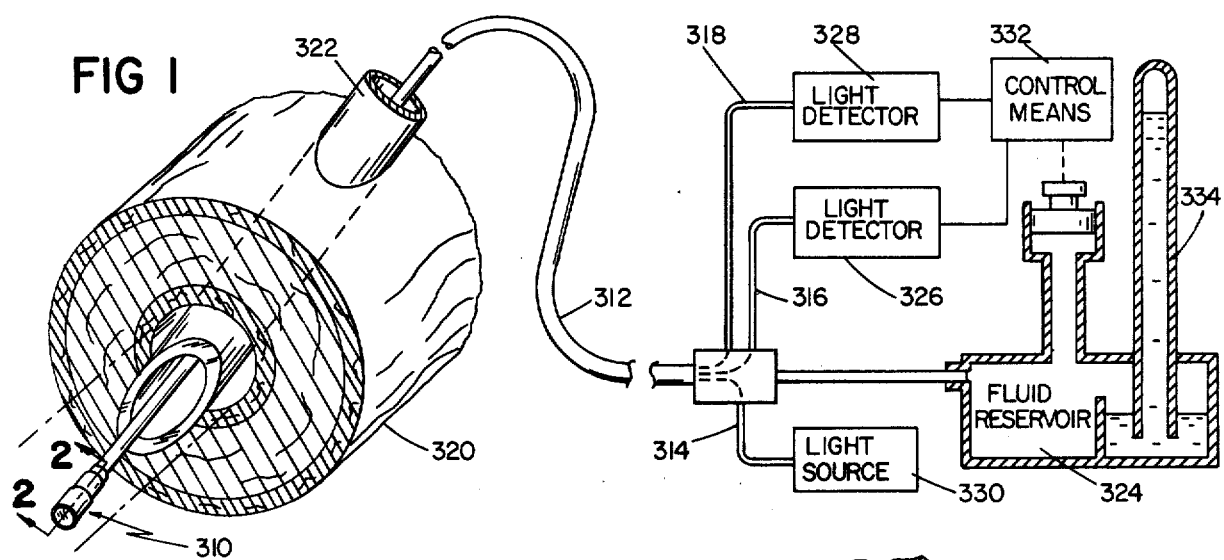
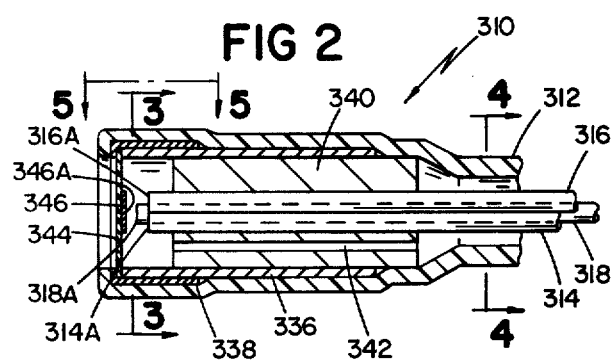
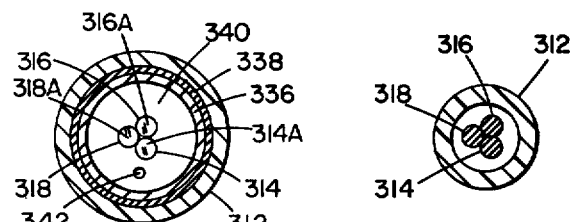
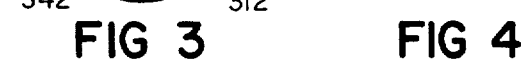
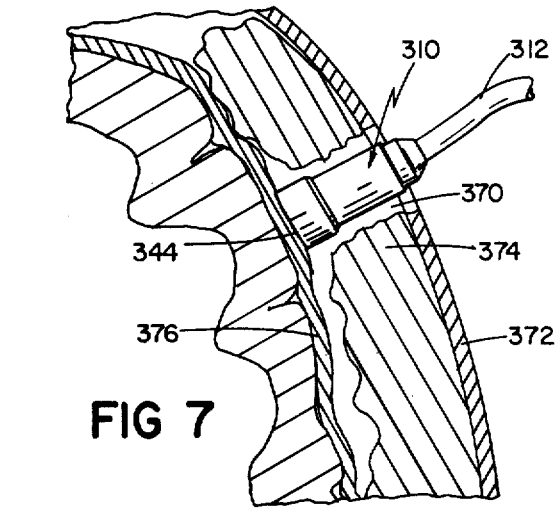
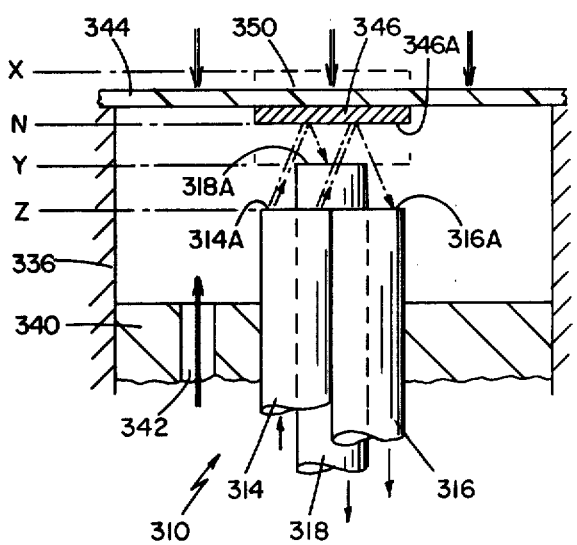
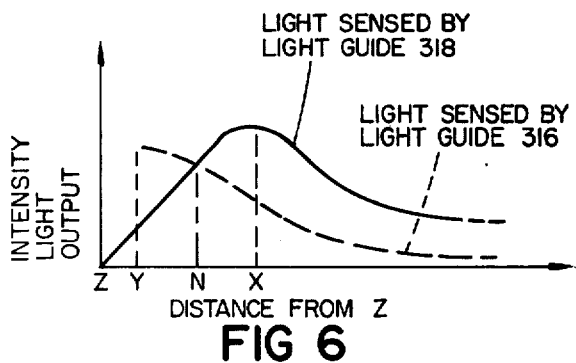

DIFFERENTIAL FIBER OPTIC DIFFERENTIAL PRESSURE SENSOR

BACKGROUND OF THE INVENTION

This invention relates to pressure measuring and monitoring devices. In particular, it relates to devices for continuously and precisely measuring pressure within a confined and relatively inaccessible space such as, but not by way of limitation, the intracranial pressure of a living human being, as exemplified in U.S. Pat. Nos. 3,686,958 and 3,789,667, whose disclosures are incorporated herein by reference, or the arterial or venous blood pressure of a living human being, or the like.

In the devices of the above mentioned patents a plurality of light guides is introduced through a pneumatic line to the interior of a flattened envelope having flexible side walls. In the U.S. Pat. No. 3,686,958 a pair of light guides is employed, one input and one output, having their internal ends facing each other and a shutter is movable by movement of a flexible side wall to modulate passage of light from one light guide end to the other with changes of relative pressure inside and outside the envelope. In the U.S. Pat. No. 3,789,667 three side by side light guides are employed, one for input of light and two for output. A reflector mounted on a side wall is arranged opposite the three internal light guide ends and moves, with movement of the side wall, in a plane parallel to the end faces of the guide so as differentially to reflect light from the input guide to the output guides. External apparatus senses the light intensities of the outputs of the output guides and, through the pneumatic line, varies the pressure in the envelope to equal that which surrounds it while at the same time displaying the pressure for monitoring purposes.

I have found that the flattened envelope configuration severely limits the minimum size of the pressure detector unit, correspondingly limiting the number of different pressure measuring and monitoring applications to which it can be put, and that sensitivity can be improved by eliminating actuation of the light modulating element by a flattened side wall and employing a new and improved arrangement and mode of operation for the differential reflection of light from the inner end of an input guide to the inner ends of two output guides.

SUMMARY OF THE INVENTION

In accordance with the invention there is provided in apparatus for monitoring ambient pressure within a confined space wherein an envelope having a flexible wall is so placed that said wall will move in response to pressure change within such space, the interior of said envelope being in communication through a fluid line with differential pressure control and display apparatus, and wherein one input light guide and two output light guides are introduced through said line and have their internal ends within said envelope, the input guide having its external end facing a light source and the output guides having their external ends facing light detectors, and means associated with the flexible wall for selectively reflecting light from the inner end of the input guide to the inner ends of the output guides in accordance with movements of said wall in response to changes in relative pressure between that in the envelope and that in the confined space, the following improvements.

The envelope comprises a rigid, generally cylindrical wall closed at one end by a generally circular, flexible end wall movable in an axial direction responsive to changes in the relative pressure, the light guides are positioned within the envelope with their internal ends facing the end wall, and the end wall carries a reflective surface facing the internal ends and movable with the end wall toward and away from the internal ends of the light guides. The internal ends are so disposed and arranged with respect to the reflective surface that when such surface is close to the internal ends a greater intensity of light from the input guide will be reflected by the surface to one of the output guides for sensing by its light detector, when the surface is remote from the internal ends, a greater intensity of the light will be reflected by the surface to the other of the output guides for sensing by its light detector, and, when the surface is in a position between its close and remote positions the reflected light will be equally intense, for correspondingly actuating said differential control and display apparatus.

In preferred embodiments the three light guides are bundled and rigidly held in the cylindrical envelope by means of a cylindrical plug which fits the envelope interior and is arranged to permit initial adjustment of the positions of the internal ends of the light guides with respect to the reflector for zero adjustment; the light guides are held within the envelope with their internal faces generally parallel to the reflective surface; the internal faces of the input light guide and one output light guide are equidistant from the reflective surface and the distance from the reflective surface to the internal face of the remaining output light guide is less than the distance to the internal faces of the other two light guides and the plug contains a fluid conducting passage between the space containing the internal ends of the light guides and the fluid line to equalize the pressure therebetween.

SHORT DESCRIPTION OF THE DRAWINGS

FIG. 1 is a largely schematic and fragmentary view of a fiber optic system for measuring blood pressure in an artery employing the novel sensor of the invention;

FIG. 2 is an enlarged longitudinal sectional view through the sensor itself taken on line 2—2 of FIG. 1 or correspondingly of FIG. 7;

FIG. 3 is a transverse section on line 3—3 of FIG. 2;

FIG. 4 is a similar section on line 4—4 of FIG. 2;

FIG. 5 is a much enlarged longitudinal sectional view of the end portion of the sensor taken on line 5—5 of FIG. 2;

FIG. 6 is a graph illustrating changes in light transmission by the two output light guides in different positions of the movable reflector of the sensor; and FIG. 7 is a view similar to FIG. 1 showing the sensor implanted for measuring intracranial pressure.

DETAILED DESCRIPTION OF PREFERRED EMBODIMENT

Referring first to FIGS. 2, 3, and 4, the novel sensor, indicated generally by numeral 310, comprises a rigid cylindrical housing 336 of suitable metal for use within a human body. It is sealed within an enlarged end portion of a flexible pneumatic tube 312 which carries loosely within it the three fiber optic light guides 314, 316, 318. The tube and guides are connected to external equipment for measuring and monitoring the pressure to be sensed and which is described in the previously mentioned earlier patents.

The light guides are bundled together and run through an axial hole in a cylindrical plug 340 which is adapted to be adjustably mounted within the housing 336. By means of a retaining ring 338 a flexible mirror supporting membrane 344 is mounted so as to close the open end of the housing 336. The light guides are held by the plug 340 with their inner ends facing the mirror 346 which is mounted for movement with the movable membrane in a direction axial of the sensor. The plug is provided with a hole 342 providing communication between the cavity bounded by the membrane 344 and the air passage provided by the tube 312. A light source 330, such as an electric lamp or light emitting diode, is arranged to focus a beam of light into the outer end of the input fiber optic 314 which transmits the same to the interior of the sensor 310. The other two fiber optics, 316 and 318, comprise output light guides to conduct light reflected from the inner end of guide 314 by the mirror 346. The bundle of light guides is adjusted so that one output guide, 318, has its inner face 318A closer to the reflector surface 346A than are faces 316A and 314A. The outer ends of guides 316 and 318 transmit the reflected light to light detectors 326 and 328.

Now if the sensor 310 is inserted in an artery 320 through syringe 322 the apparatus is ready to measure and monitor blood pressure on a continuous basis. The mode of operation will be best understood from a consideration of FIGS. 5 and 6.

The membrane 344, carrying the reflector 346, can move between extreme outer position X and extreme inner position Y, the distances being measured between the face 318A of guide 318 and the surface 346A of the mirrow 346 as indicated on the graph FIG. 6. If the pressure external to the sensor is greater than that within the sensor the membrane moves toward Y. If such pressure is less than that within the unit the membrane moves toward X. When the pressures are equalized the membrane takes neutral position N.

Now, considering FIG. 6, the abscissa represents distance of the mirror surface 346A from the faces 314A and 316A of the corresponding light guides. The ordinates depict the intensity of reflected light received by and transmitted to the external apparatus by the guides at different distances along the abscissa, yielding two curves which intersect at N, the position when the two light outputs are equal. At the extreme inner position Y the mirror face contacts or is so close to face 318A that essentially no light is reflected to guide 318, as indicated at Y on the graph. At this position, maximum light is reflected to output guide 316. As the mirror moves away from the inner ends of the guides the intensity of light reflected to guide 316 decreases and that reflected to guide 318 increases, following the square law equation concerning illumination from a point source. At N the outputs of guides 316 and 318 are equal. At positions approaching X guide 318 receives, and hence transmits, more light than does guide 316.

By coupling the outputs of guides 316 and 318 to a pair of photocells in detectors 326 and 328 connected in a differential configuration electrically, the relative intensity of the light outputs of the two fibers may be used to drive a servo mechanism which can either increase or decrease the internal fluid pressure within the sensor through tube 312, hence tending to move the membrane toward its neutral position N. Thus, the pressure within tube 312 becomes a measure of the pressure sensed by the unit within artery 320, all as described in said prior U.S. Pat. No. 3,789,667. Very briefly, the differential electrical output of the pair of light detectors 326, 328 actuates control means 332 which, in turn, increases or decreases air pressure in fluid reservoir 324 which pressure may be read out on manometer 334. Membrane 344, in turn moves toward position N at which point the read-out indicates the pressure being monitored, such as blood pressure.

FIG. 7 discloses the use of the novel sensor for monitoring intracranial pressure. The cylindrical unit 310 is mounted in burr hole 370 in the patient's skull 374 and opening in scalp 372. The external face of membrane 344 is positioned against the dura 376. The mode of operation remains the same as that already described.

In preferred embodiments adapted for the measurement of pressure within the skull of a living human being the sensor unit is ¼ inch in diameter and ⅜ inch long. The flexible tubing has an outside diameter of 1/16 inch. The fiber optic light guides, which are carried within the flexible tubing between the unit and the external apparatus are composed of a plurality of flexible light-conducting fibers, bundled together, and have a diameter of about ten mils or ten-thousandths of an inch (0.010 inch).

Because of the novel improved configuration of the sensor it is capable of being scaled down for assembly under a microscope to be as little as 1/16 inch in diameter and be ¼ inch long. These smaller models would not be limited to taking blood pressure readings in situ in major blood vessels but could be used throughout the greater part of the circulatory system, including the heart. If this sensor is enclosed in an adaptor chamber which is connected to a syringe needle inserted into the spinal column, then spinal fluid pressures may be determined. This chamber-needle adaptor can be used to determine arterial or venous blood pressures wherever the vessels themselves are readily accessible nearer the surface of the body or also to determine amniotic fluid pressure simultaneously with fluid sampling for analytical purposes.

Other advantageous applications of the preferred embodiment include: spinal fluid pressure as previously described; a modification to the read-out system to add counting the time between pressure changes as well as balance of pressure changes, to monitor the breathing of new-born infants; monitoring intracranial pressure of new-born infants non-invasively from the external surface of the fontanel by lightly pressing the flexible membrane of the sensor against the skin; eye ball or cornea pressure measuring by pressing the flexible membrane against the appropriate area; amniotic fluid pressure measuring without perforating the amniotic membrane, thereby avoiding the attendant problems such as fluid seepage, membrane rupture, and the spread of disease organisms; and pressure measurement through any flexible membrane against which the sensor can be placed.

The materials used in and in making the novel sensor may vary in accordance with the intended applications. For low pressures such as physiological pressure of the human body the fluid may be air or gas, the fiber optic light guides plastic or glass, the flexible membrane of medical grade silicone and the flexible air tube of medical grade, non-alergenic vinyl plastic. For applications involving higher pressures or a more severe environment a suitable transparent liquid may be substituted for air or gas and the light guides may be glass or quartz while the resilient membrane can be made of resilient metal.

Whenever ambient light can leak through the fluid line and thense into the light guides or into the inner sensor chamber, the light source can be pulsed or "chopped." Only the pulse outputs of the photodetectors are transmitted to the servo-mechanism electronics, thus steady-state outputs from the photodetectors caused by ambient light do not cause erroneous readings or read-out zero shift.

I claim:

1. In apparatus for monitoring ambient pressure within a confined sapce wherein an envelope having a flexible wall is so placed that said wall will move in response to pressure change within such space, the interior of said envelope being in communication through a fluid line with differential pressure control and display apparatus, and wherein one input light guide and two output light guides are introduced through said line and have their internal ends within said envelope, the input guide having its external end facing a light source and the output guides having their external ends facing light detectors, and means associated with the flexible wall for selectively reflecting light from the inner end of the input guide to the inner ends of the output guides in accordance with movements of said wall in response to changes in relative pressure between that in the envelope and that in the confined space, the improvement wherein said envelope comprises a rigid, generally cylindrical wall closed at one end by a generally circular, flexible end wall movable in an axial direction responsive to changes in said relative pressure, said light guides are positioned within said envelope with their internal ends facing said end wall, and said end wall carries a reflective surface facing said internal ends and movable with said end wall toward and away from said internal ends, said internal ends being so disposed and arranged with respect to said reflective surface that when said surface is close to said internal ends a greater intensity of light from the input guide will be reflected by the surface to one of said output guides for sensing by its light detector, when said surface is remote from said internal ends, a greater intensity of said light will be reflected by said surface to the other of said output guides for sensing by its light detector, and, when said surface is in a position between said close and remote positions the reflected light will be equally intense, for correspondingly actuating said differential control and display apparatus.

2. The apparatus as claimed in claim 1 wherein the internal portions of said light guides are positioned by means of a cylindrical plug fitting within said envelope and arranged to permit adjustment of the positions of the light guide ends with respect to said reflecting surface for zero adjustment.

3. Apparatus as claimed in either claim 1 or claim 2 wherein the internal end of one of said output light guides is positioned closer to said reflecting surface than are the ends of the other two light guides whereby said reflecting surface will reflect more light to one output guide than to the other when it is in a position close to their ends, the reverse will be true when said surface is in a position further from said ends and said surface will reflect equal intensities of light to each output guide when said surface is in a position between said two positions.

4. Apparatus in accordance with either claim 2 or 3 wherein said plug is provided with a fluid conducting passage between the space containing the internal end of said light guides and said fluid line to equalize the pressure therebetween.

* * * * *